United States Patent
O'Lenick, Jr.

(10) Patent No.: US 9,497,962 B1
(45) Date of Patent: Nov. 22, 2016

(54) HYDROALCOHOLIC FOAMING SANITIZER

(71) Applicant: Anthony J. O'Lenick, Jr., Dacula, GA (US)

(72) Inventor: Anthony J. O'Lenick, Jr., Dacula, GA (US)

(73) Assignee: S.LTECH LLC, Lawrenceville, GA (US)

( * ) Notice: Subject to any disclaimer, the term of this patent is extended or adjusted under 35 U.S.C. 154(b) by 383 days.

(21) Appl. No.: 14/120,674

(22) Filed: Jun. 16, 2014

Related U.S. Application Data

(60) Provisional application No. 61/964,121, filed on Dec. 24, 2013.

(51) Int. Cl.
*A01N 25/32* (2006.01)
*A01N 31/02* (2006.01)

(52) U.S. Cl.
CPC .............. *A01N 25/32* (2013.01); *A01N 31/02* (2013.01)

(58) Field of Classification Search
CPC .............................. A01N 25/16; A01N 25/32
USPC ................................. 514/63, 724; 424/404
See application file for complete search history.

(56) References Cited

U.S. PATENT DOCUMENTS

| | | | | |
|---|---|---|---|---|
| 5,288,486 A | * | 2/1994 | White | A01N 25/24 424/78.07 |
| 5,635,462 A | * | 6/1997 | Fendler | A01N 31/08 510/123 |
| 5,997,893 A | * | 12/1999 | Jampani | A61K 8/34 424/401 |
| 6,022,551 A | * | 2/2000 | Jampani | A01N 31/16 424/401 |
| 6,136,771 A | * | 10/2000 | Taylor | C11D 3/3418 510/130 |
| 6,228,385 B1 | * | 5/2001 | Shick | A61K 8/0208 424/409 |
| 6,423,329 B1 | * | 7/2002 | Sine | A61K 8/26 424/401 |
| 6,723,689 B1 | * | 4/2004 | Hoang | A01N 31/02 424/404 |
| 8,691,255 B2 | * | 4/2014 | Fernandez de Castro | A01N 25/06 424/1.65 |

* cited by examiner

*Primary Examiner* — Porfirio Nazario Gonzalez

(57) ABSTRACT

The present invention is related to an improved method of foaming hydroalcoholic solutions having between 60% and 80% ethanol (by weight) present. The compositions of the present invention are useful as hand sanitizer compositions. The compositions of the present invention provide copious dense foam, and an outstanding skin feel upon evaporation of the water and alcohol.

8 Claims, No Drawings

HYDROALCOHOLIC FOAMING SANITIZER

RELATED APPLICATION

This application claims priority to and benefit of U.S. Provisional Application No. 61/964,121 filed Dec. 24, 2013, the disclosure of which is incorporated herein for all purposes.

FIELD OF THE INVENTION

The present invention is related to an improved method of foaming hydroalcoholic solutions having between 60% and 80% ethanol (by weight) present. The compositions of the present invention are useful as hand sanitizer compositions. The compositions of the present invention provide copious dense foam, and an outstanding skin feel upon evaporation of the water and alcohol.

BACKGROUND OF THE INVENTION

Various forms of antimicrobial compositions containing alcohols are known in the art and have been used in the healthcare industry for some time. The antimicrobial compositions are typically utilized to cleanse the skin and destroy bacteria and other microorganisms present thereon, especially on the hands, arms, and face of the user.

An important use of the antimicrobial composition is to disinfect the hands and fingers of a person. The composition is generally applied to, and rubbed into the hands and fingers, and subsequently allowed to evaporate from the skin. Wiping of the composition from the skin is typically not necessary because of the alcohol content of the compositions, which leads to fast and essentially complete evaporation of the composition from the skin.

Antimicrobial compositions in general have been used in the healthcare industry, food service industry, meat processing industry, and in the private sector by individual consumers to control and prevent the spread of potentially harmful microorganisms. The widespread use of antibacterial compositions indicates the importance of controlling bacteria and other microorganism populations on the skin or other substrates. It is important, that the antimicrobial compositions reduce microorganism populations rapidly, without irritating or damaging skin or having a detrimental toxicity. The prior art antimicrobial compositions generally contain a high percentage of alcohol, wherein the alcohol acts as a disinfectant, which rapidly evaporates preventing the need to wipe or rinse the composition from the treated surface. However, it has been found that high amounts of alcohol generally greater than about 60% dry and/or irritate skin.

U.S. Pat. No. 5,288,486 relates to a process for enhancing the efficacy of alcohol-based skin antiseptics comprising adding at least one alcohol-soluble viscosifying agent to an alcohol-based disinfectant, thereby lowering its alcohol evaporation rate and markedly increasing the exposure time that disinfecting concentrations of alcohol are present on skin.

U.S. Pat. No. 5,635,462 relates to a reportedly cleansing composition including a substituted phenol such as para-chloro-meta-xylenol, and at least one primary surfactant selected from the group consisting of amine oxides, phospholipids, partially neutralized carboxylic acids and diacids, betaines, ethoxylated methyglucosides, and mixtures thereof. Other additives such as viscosifiers or thickeners, emollients, fragrances, perfumes, coloring agents, and the like may also be added.

U.S. Pat. No. 5,997,893 relates to reportedly antimicrobial compositions containing high levels of alcohol, carbomer polymers and antimicrobial agents which provide formulations possessing cosmetic characteristics.

U.S. Pat. No. 6,022,551 relates to reportedly antimicrobial alcohol-containing composition and method of using the composition to reportedly disinfect surfaces, such as the hands is disclosed.

U.S. Pat. No. 6,136,771 relates to reportedly antibacterial compositions having a reduced amount of disinfecting alcohol. The antibacterial compositions contain a phenolic antibacterial agent, a disinfecting alcohol, a gelling agent, and water, wherein a percent saturation of the antibacterial agent in a continuous aqueous phase of the composition is at least 25%.

U.S. Pat. No. 6,228,385 relates to a liquid reportedly antimicrobial, skin moisturizing formulation including: 1) an aqueous alcoholic base; 2) a humectant; 3) a delivery material adapted to release an emollient when the formulation is applied to the skin; and 4) an emollient immiscible in the aqueous alcoholic base and contained by the delivery material. The delivery material reportedly encapsulates or entraps the emollient for subsequent release. Desirably, the humectant is glycerin and the emollient is an alkyl-substituted polysiloxane polymer.

U.S. Pat. No. 6,423,329 relates to compositions and methods of sanitizing and moisturizing skin surfaces.

U.S. Pat. No. 6,723,689 relates to a reportedly antimicrobial composition comprising an alcohol in an amount from about 60 to about 95 weight percent of the total composition, a preservative, a cationic cellulose polymer thickening agent, a moisturizer and/or a cationic emulsifier, and water in an amount from about 6 to about 30 weight percent.

A variety of patents exist that describe the use of dimethicone copoylol compounds to foam alcohol sanitizers. The most preferred material described in these patents is Example 1 below.

Prior to the current invention, patents dealing with the use of dimethicone copolyol as hydro alcoholic foaming agents, for use in sanitizer compositions, did not recognize that there are advantages that can be derived from using silicone quaternary compounds if (a) foaming hydroalcoholic solutions (b) improving the feel of said formulations, and (c) providing a bacteriostatic compound to the skin that survives the evaporation of the alcohol.

The selection of the proper silicone quaternary compound results in improved efficiency formulations.

The ability to foam hydro alcoholic solutions depends upon is dictated in part by the surface tension of the hydro alcoholic solution, which in turn is related to the concentration of ethanol in the solution.

| % Ethanol (Wt) | Surface Tension Dynes/Cm |
| --- | --- |
| 60 | 27.72 |
| 70 | 26.37 |
| 80 | 25.28 |
| 100 | 22.39 |

As seen above, as the % Ethanol increases, the surface tension decreases. The relationship is almost linear over a range of 60% to 100%

THE INVENTION

Object of the Invention

It is the object of the resent invention to provide a foaming hydroalcoholic solution having at least 65% ethanol which provides a stable tight foam, a light not sticky skin feel after evaporation of the alcohol and water, and a non-volatile bacteria stat which provides protection to the skin for longer than it takes for the evaporation needs to be completed.

Other objects will become apparent from reading the specification.

All percentages cited are percentages by weight, all temperatures are degrees C. and all patents referenced herein are incorporated herein by reference as allowed.

SUMMARY OF THE INVENTION

We have discovered that specific silicone quaternary compounds provide enhanced properties when added to hydro alcoholic solutions at a concentration of between 1 and 5% by weight. Improvement in foam thickness, skin feel and providing a formulation that will provide bacteriostatic properties to the skin after the alcohol evaporates can be achieved using the compositions of the present invention. The first of two requirements is that the silicone quaternary used in the hydro alcoholic solution, must have a terminal, must be able to reduce the surface tension of the hydro-alcoholic solution to be operative, and must have a defined structure chosen to insure the solubility of the silicone quaternary in the hydro-alcoholic solution. Too much silicone in the molecule renders the resulting silicone quaternary compound insoluble it the hydro-alcoholic solution.

It is critical to the functionality of the current invention that the silicone quaternary compounds have a terminal structure as shown:

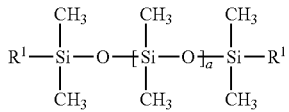

wherein:
$R^1$ is

This class of compounds works in the present invention while the internal substitution pattern does not provide acceptable foam, skin feel or prolonged efficacy.

The non-functional silicone quaternary compounds are internally functionalized (so called comb structures) and have the following structure;

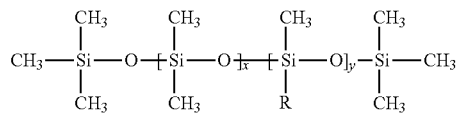

wherein:
R is

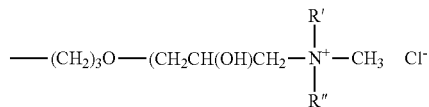

wherein;
R' and R" are selected from the group consisting of —$CH_3$ and —$CH_2CH_3$.

The compositions of the present invention are made using a terminal silicone quaternary compound with the proper value for "a".

DETAILED DESCRIPTION OF THE INVENTION

A foaming alcohol composition that comprises:
(a) between 1% and 5% by weight of a silicone polymer conforming to the following structure:

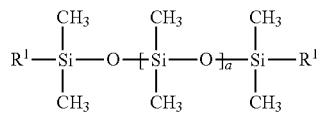

wherein:
$R^1$ is

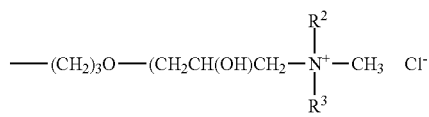

a is an integer ranging from 8 to 25;
$R^2$ and $R^3$ are selected from the group consisting of —$CH_3$ and —$CH_2CH_3$;
(b) between 60 and 80% ethanol by weight;
(c) between 39 and 15% water by weight.

Another aspect of the present invention is a process for sanitizing the skin which comprises contacting the skin with a composition comprising;
(a) between 1% and 5% by weight of a silicone polymer conforming to the following structure:

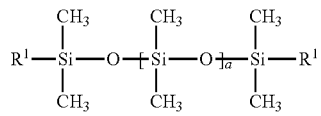

wherein:
$R^1$ is

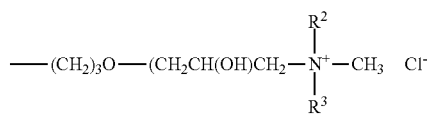

a is an integer ranging from 8 to 25;
$R^2$ and $R^3$ are selected from the group consisting of —$CH_3$ and —$CH_2CH_3$;
(b) between 60 and 80% ethanol by weight;
(c) between 39 and 15% water by weight.

PREFERRED EMBODIMENT

In a preferred embodiment a is 10.
In a preferred embodiment a is 20.
In a preferred embodiment a is 25.
In a preferred embodiment a is 60.
Testing—Cylinder Shake Foam Test
The cylinder shake foam test is used to measure amount of foam produced by a specific sample in water or other solution.
Principle
A sample comprising 1% of the test silicone, 65% anhydrous ethanol and 34% water by weight is prepared. 50 ml of solution is added to a 100 ml graduated cylinder, and shaken for five seconds. The height of foam is measured initially after shaking, and after one and three minutes on standing.
Apparatus
Graduated Cylinder, 100 ml, with stopper.
Procedure
1. Make a stock solution of 1% sample in water, or the desired solution, at 25 C. Mix gently so as to not create any foam.
2. Add the 1% sample stock solution to a 100 ml graduated cylinder so that it is at exactly the 50 ml mark. Firmly place a stopper on the mouth of the cylinder. With thumbs on the stopper to prevent it from coming loose (do not use grease to lubricate the stopper as this can act as a defoamer), shake vigorously for five seconds.
3. Carefully release pressure if necessary.
4. Immediately after shaking, measure the top level of the foam phase and the top level of the water phase in ml.
5. Measure again after one and three minutes on standing.
6. Repeat three times and average the results.
Calculation:
Height of foam is equal to the top level of foam (ml) minus the top level of water layer (ml).

EXAMPLES

Example 1

The following compound is commercially available from Siltech Corporation, Toronto Ontario Canada and is widely used in the foaming of hydroalcoholic solutions;

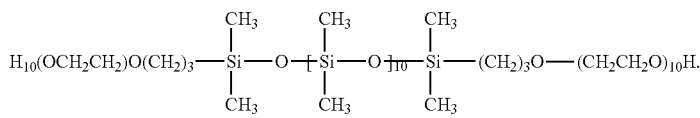

Example 2-5

The polymers useful in making the compositions of the present invention have the following structure;

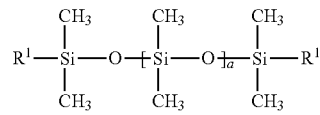

wherein:
$R^1$ is

| Example | $R^2$ | $R^3$ | a |
|---|---|---|---|
| 2 | —$CH_2$—$CH_3$ | —$CH_2$—$CH_3$ | 10 |
| 3 | —$CH_2$—$CH_3$ | —$CH_2$—$CH_3$ | 20 |
| 4 | —$CH_2$—$CH_3$ | —$CH_2$—$CH_3$ | 25 |
| 5 | —$CH_2$—$CH_3$ | —$CH_2$—$CH_3$ | 50 |

Examples 6-7

Comb Structures

Comb polymers have the following structure;

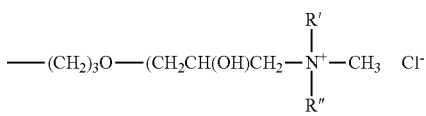

wherein:
R is

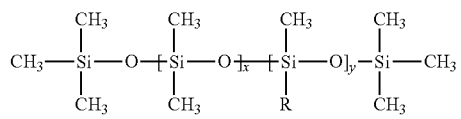

wherein;
R' and R" are —CH$_2$CH$_3$.

| Example | R' | R" | x | y |
|---|---|---|---|---|
| 6 | —CH$_2$—CH$_3$ | —CH$_2$—CH$_3$ | 4 | 9 |
| 7 | —CH$_2$—CH$_3$ | —CH$_2$—CH$_3$ | 10 | 20 |

Results

|  | 0 min. Foam Height ml | 1 min. Foam Height ml | 2 min. Foam Height Ml | 3 min. Foam Height ml |
|---|---|---|---|---|
| Control |  |  |  |  |
| Example 1 Present Invention | 101.7 | 71.0 | 61.3 | 54.3 |
| Example 2 | 97.0 | 69.3 | 61.3 | 55.0 |
| Example 3 | 90.3 | 58.7 | 51.7 | 48.5 |
| Example 4 | 93.3 | 58.7 | 54.3 | 49.3 |
| Example 5 Internal Quats | 85.0 | 49.7 | 44.7 | 41.3 |
| Example 6 | 70.0 | 21.0 | 8.7 | 3.2 |
| Example 7 | 64.7 | 14.3 | 10.0 | 6.7 |

An acceptable foam level is defined by consumers as above 80 on initial foam.

The skin feel was also evaluated by panelists. They were asked to describe the feel of the product after the alcohol evaporated.

| Feel Evaluation | |
|---|---|
| Control |  |
| Example 1 Present Invention | Sticky |
| Example 2 | Dry |
| Example 3 | Dry |
| Example 4 | Light feel |
| Example 5 | Conditioning Feel, non sticky |

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A composition comprising;
   (a) between 1% and 5% by weight of a silicone polymer conforming to the following structure:

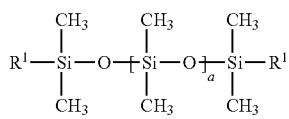

wherein:
R' is

a is an integer ranging from 8 to 25;
R$^2$ and R$^3$ are selected from the group consisting of —CH$_3$ and —CH$_2$CH$_3$;
   (b) between 60 and 80% ethanol by weight;
   (c) between 39 and 15% water by weight.

2. A composition of claim 1 wherein a is 10.
3. A composition of claim 1 wherein a is 20.
4. A composition of claim 1 wherein a is 25.
5. A process for sanitizing the skin which comprises contacting the skin with a composition comprising;
   (a) between 1% and 5% by weight of a silicone polymer conforming to the following structure:

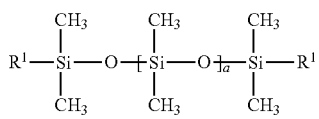

wherein:
R$^1$ is

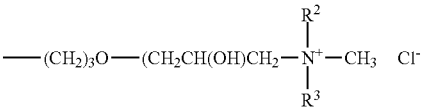

a is an integer ranging from 8 to 25;
R$^2$ and R$^3$ are selected from the group consisting of —CH$_3$ and —CH$_2$CH$_3$;
   (b) between 60 and 80% ethanol by weight;
   (c) between 39 and 15% water by weight.

6. The process of claim 5 wherein a is 10.
7. The process of claim 5 wherein a is 20.
8. The process of claim 5 wherein a is 25.

* * * * *